United States Patent [19]
Mount et al.

[11] 4,092,269
[45] May 30, 1978

[54] PHOSPHORUS-VANADIUM-OXYGEN CATALYSTS HAVING A SPECIFIC PORE VOLUME

[75] Inventors: Ramon A. Mount, St. Louis; John F. Pysz, Jr., Crestwood; Harold Raffelson, Olivette, all of Mo.

[73] Assignee: Monsanto Company, St. Louis, Mo.

[21] Appl. No.: 732,555

[22] Filed: Oct. 15, 1976

[51] Int. Cl.$^2$ .................. B01J 27/14; C07D 307/60
[52] U.S. Cl. ................................ 252/435; 252/437; 260/346.75
[58] Field of Search ........................... 252/435, 437

[56] References Cited

U.S. PATENT DOCUMENTS

| B 330,354 | 1/1975 | Mount et al. | 252/435 X |
|---|---|---|---|
| 2,054,865 | 9/1936 | Oxley et al. | 252/435 X |
| 2,738,336 | 3/1956 | Mavity | 252/435 |
| 3,156,706 | 11/1964 | Kerr | 252/437 X |
| 3,183,196 | 5/1965 | Watanabe et al. | 252/456 |
| 3,293,268 | 12/1966 | Bergman et al. | 252/437 X |
| 3,888,886 | 6/1975 | Young et al. | 252/435 X |
| 3,915,892 | 10/1975 | Harrison | 252/435 |
| 3,985,775 | 10/1976 | Harrison | 252/437 X |
| 3,987,063 | 10/1976 | Lemal et al. | 252/437 X |

*Primary Examiner*—Winston A. Douglas
*Assistant Examiner*—William G. Wright
*Attorney, Agent, or Firm*—J. C. Logomasini; P. L. Passley; S. M. Tarter

[57] ABSTRACT

The prior art discloses that phosphorus-vanadium-oxygen catalysts wherein the phosphorus to vanadium atom ratio is between about 1:2 and about 2:1, and wherein at least about 20 atom percent of the vanadium is in the tetravalent state, are useful for the conversion of aliphatic hydrocarbons to maleic anhydride. It has now been found that when the pore volume of the catalysts from pores having diameters between about 0.8 micron and about 10 microns is greater than 0.02 cc/g, the catalyst is particularly useful for the conversion of saturated hydrocarbons, such as butane, to maleic anhydride.

5 Claims, No Drawings

PHOSPHORUS-VANADIUM-OXYGEN CATALYSTS HAVING A SPECIFIC PORE VOLUME

BACKGROUND OF THE INVENTION

This invention relates to a method for preparing catalysts useful in the manufacture of maleic anhydride by the oxidation of aliphatic hydrocarbons, and more particularly it is directed to catalysts suitable for producing maleic anhydride from saturated hydrocarbons in higher yields than heretofore possible.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs.

The prior art discloses a number of catalysts useful for the conversion of organic feedstocks to maleic anhydride. As an example, U.S. Pat. No. 3,293,268 teaches a process of oxidizing saturated aliphatic hydrocarbons to maleic anhydride under controlled temperature conditions in the presence of a phosphorus-vanadium-oxygen catalyst. U.S. Pat. No. 3,864,280 discloses a phosphorus-vanadium-oxygen catalyst prepared by a method employing an organic solvent to provide a catalyst having a surface area between about 7 and about 50 m$^2$/g. U.S. Pat. No. 3,915,892 relates to the preparation of a phosphorus-vanadium-oxygen catalyst using a carefully controlled sequence of steps to heat the precursor to prepare the catalyst. Numerous references are in the prior art relating to phosphorus-vanadium-oxygen catalysts containing a small amount of a promoting element to enhance the yield of maleic anhydride.

Although the prior art catalysts provide acceptable yields of maleic anhydride, it has now been found that the yield of maleic anhydride using a phosphorus-vanadium-oxygen catalyst is significantly improved by controlling the pore size distribution in the finished catalyst. The improved yields of maleic anhydride that are achieved using the catalyst of the present invention wherein the pore size distribution is controlled are far superior to the prior art catalysts.

SUMMARY OF THE INVENTION

These and other advantages are achieved by a catalyst which comprises phosphorus, vanadium and oxygen, wherein the phosphorus to vanadium atom ratio is between about 1:2 and about 2:1, wherein at least about 20 atom percent of the vanadium is in the tetravalent state, and wherein the pore volume of the catalyst from pores having diameters between about 0.8 micron and about 10 microns is greater than about 0.02 cc/g. Such a catalyst can be made in a method of preparing a phosphorus-vanadium-oxygen catalyst wherein a phosphorus compound and a vanadium compound are brought together under conditions to provide a catalyst precursor having a phosphorus to vanadium atom ratio between about 0.5:1 and 2:1, and calcining the precursor at a temperature between about 300° and 600° C., the improvement which comprises adding to the precursor a sufficient amount of a pore modification agent to provide a catalyst wherein the pore volume from pores having diameters between about 0.8 micron and about 10 microns is greater than 0.02 cc/g.

For the purposes of this invention, the term "pore modification agent" shall mean any material or combination of materials that can be removed from a phosphorus-vanadium-oxygen catalyst precursor by decomposition, evaporation, sublimation, combustion, melting, leaching and the like, and does not react adversely with the precursor or the resultant catalyst. The term "yield" means the ratio of the moles of maleic anhydride obtained to the moles of feed introduced into the reaction. The term "space velocity" means the hourly volume of gaseous feed expressed in cubic centimeters (cc) at 15.5° C. and standard atmospheric pressure, divided by the catalyst bulk volume, expressed in cubic centimeters (cc), the term expressed as cc/cc/hr.

CATALYST PREPARATION

Broadly described, the catalysts of this invention are prepared by bringing together a phosphorus compound and a vanadium compound under conditions to provide a catalyst precursor having a phosphorus to vanadium atom ratio between about 0.5:1 and about 2:1, and having greater than 50 atom percent of the vanadium in the tetravalent state. The catalyst precursor is then formed into structures for use in a maleic anhydride reactor. A pore modification agent is added at any stage prior to calcination. Thereafter, the structured catalyst precursor containing the pore modification agent is calcined at a temperature between about 300° and 600° C.

The vanadium compounds useful as a source of vanadium in the catalyst precursors are those known to the art. Suitable vanadium compounds include: vanadium oxides, such as vanadium pentoxide, vanadium trioxide, and the like; vanadium oxyhalides, such as vanadyl chloride, vanadyl dichloride, vanadyl trichloride, vanadyl bromide, vanadyl dibromide, vanadyl tribromide, and the like; vanadium-containing acids, such as metavanadic acid, pyrovanadic acid, and the like; vanadium salts, such as ammonium metavanadate, vanadium sulfate, vanadium phosphate, vanadyl formate, vanadyl oxalate, and the like. However, vanadium pentoxide is preferred.

The phosphorus compounds useful as a source of phosphorus in the catalyst precursor are also those known to the art. Suitable phosphorus compounds include: phosphoric acid, such as metaphosphoric acid, orthophosphoric acid, and the like; phosphorus pentoxide; phosphorus halides, such as phosphorus oxyiodide, phosphorus pentachloride, phosphorus oxybromide, and the like; compounds commonly known as trivalent phosphorus compounds such as phosphorous acid, phosphorus trihalides; organic phosphites, sometimes known as phosphonates, (e.g., trimethyl phosphite), and the like. However, phosphoric acid and phosphorus pentoxide are preferred, and a mixture of phosphoric acid and phosphorous acid is especially preferred.

To prepare the catalyst precursors by the process of the present invention, a vanadium compound is brought together with a phosphorus compound in an acid solution and the mixture is heated to dissolve the starting materials. A reducing agent is used to reduce pentavalent vanadium to tetravalent vanadium and to maintain the vanadium in the tetravalent state. As is well known to those skilled in the art, hydrogen halide acid or oxalic acid solutions, which are mild reducing agents, can serve not only as the acid but also as the reducing agent for the pentavalent vanadium. On the other hand, a trivalent phosphorus compound can be used to provide tetravalent vanadium and also serve as a source of phosphorus to provide the catalyst precursor. It is preferred to use phosphorous acid as the trivalent phosphorus compound which serves as an acid medium to provide the tetravalent vanadium in the precursor. The acid solution containing the phosphorus compound and the vanadium compound is heated until a blue solution is obtained, indicating that at least 50 atom percent of the vanadium is in the tetravalent state. The amount of time required to dissolve the phosphorus compound and the vanadium compound and to provide a substantial amount of the vanadium in the tetravalent state and to provide the catalyst precursors varies from batch to batch, depending upon the compounds used as starting materials and the temperature at which the compounds are heated. In general, however, heating the solution to at least 100° C. for about 4 hours is sufficient. However, as will occur to those skilled in the art, an aliquot of the solution can be analyzed to insure that at least 50 atom percent of the vanadium is in the tetravalent state.

The atom ratio of phosphorus to vanadium in the starting materials is important since it controls the phosphorus to vanadium atom ratio in the final catalyst. When phosphorus-vanadium-oxygen precursors contain a phosphorus to vanadium atom ratio below about 0.5:1 or above about 2:1, the yield of maleic anhydride using the catalyst prepared from these precursors is so low that it is not of commercial significance. It is preferred that phosphorus-vanadium-oxygen precursors have a phosphorus to vanadium atom ratio between about 1:1 and about 1.5:1. When the catalyst is used to convert a feed that is primarily butane to maleic anhydride, it is even more preferable that the precursor have a phosphorus to vanadium atom ratio between about 1:1 and about 1.1:1.

After the vanadium and phosphorus compounds are brought together and a substantial amount of the vanadium is in the tetravalent state, it is necessary to recover the phosphorus-vanadium-oxygen precursors. Techniques for recovering the phosphorus-vanadium-oxygen precursors are well known to those skilled in the art. For example, the precursors can be deposited from aqueous solution on a carrier, such as alumina or titania, or the precursors can be dried by gentle heating to provide solid phosphorus-vanadium-oxygen precursors.

In the process of the present invention, the pore modification agent can be added at any stage of the preparation prior to calcination of the phosphorus-vanadium-oxygen precursor to form the catalyst of the present invention. As an example, the pore modification agent can be added when the vanadium compound is brought together with the phosphorus compound to provide the precursor. Alternatively, the pore modification agent can be added to the solution of the precursor before it is deposited on a carrier or dried to provide solid phosphorus-vanadium-oxygen precursors containing the pore modification agent. On the other hand, the pore modification agent can be added to the solid phosphorus-vanadium-oxygen precursor by blending the pore modification agent with the ground precursor before it is tabletted or prilled prior to calcination, and this is what we prefer to do.

The amount of pore modification agent to be added to the catalyst precursor can vary within wide limits. When less than about 1 weight percent pore modification agent, based on the weight of the dry precursor, is added to the precursor, the increase in pore volume of the catalyst resulting from pores having diameters between about 0.8 micron and about 10 microns is increased only slightly. On the other hand, the use of more than about 30 weight percent pore modification agent does not seem to have a beneficial result on the resulting catalyst, and in some cases, may have a deleterious effect on the yield of maleic anhydride using such a catalyst. It is preferred to use between about 2 weight percent and about 15 weight percent of the pore modification agent, based on the weight of the dry precursor.

The exact mechanism by which pore modification agents will increase the pore volume of the catalyst resulting from pores having diameters between about 0.8 and about 10 microns is not understood at this time. A number of materials known to the art can be used as pore modification agents to provide satisfactory results. It is only necessary that the pore modification agent does not react adversely with the phosphorus-vanadium-oxygen precursor or the resulting catalyst, and can be removed from the catalyst during calcination by thermal decomposition, volatilization, sublimation and the like, to provide a catalyst having a pore volume greater than 0.02 cc/g, from pores having diameters between about 0.8 micron and about 10 microns.

Suitable pore modification agents include: organic acids, such as adipic acid, citric acid, oxalic acid, stearic acid and the like; polymeric materials such as polyethylene glycol having a molecular weight of about 6,000, polyvinyl alcohol, polyacrylic acid and the like; cellulosic materials, such as ground cellulose, methylcellulose, pecan shell flour, cherry shell flour, walnut shell flour and the like; monosaccharides and polysaccharides, such as various sugars, corn starch, soluble starch and the like; and other products derived from nature, such as hydrogenated vegetable oils, waxes, gelatin and the like. Mixtures of such materials are also satisfactory. On the other hand, graphite, which is commonly used as a pelletizing lubricant when forming tablets of a phosphorus-vanadium-oxygen precursor or catalyst, is not satisfactory as a pore modification agent in the process of the present invention, although its presence is not harmful. Cellulosic materials and hydrogenated vegetable oils are preferred, and methylcellulose is especially preferred.

The phosphorus-vanadium-oxygen precursors containing the pore modification agent are then formed into structures suitable for use in a maleic anhydride reactor. Techniques for forming appropriate structures from precursors for use in a fluidized bed reactor or in a fixed-tube, heat-exchanger type reactor are well known to those skilled in the art. For example, the precursor containing the pore modification agents can be structured for use in a fluidized bed reactor by depositing the phosphorus-vanadium-oxygen precursor containing the pore modification agent on a carrier. Alternately, dried precursors containing the pore modification agent can be comminuted for use in the fluidized bed reactor. On the other hand, precursors can be structured for use in a fixed-tube, heat-exchanger type reactor by extruding a paste of the precursor containing the pore modification agent through an orifice, or by prilling or tabletting the precursors containing the pore modification agent.

After the phosphorus-vanadium-oxygen precursors containing the pore modification agent are formed into structures which will be used in a maleic anhydride reactor, the precursors are then calcined at temperatures between about 300° and about 600° C. for at least two hours to provide the catalysts of the present invention. It is preferred to convert part of the tetravalent vanadium to pentavalent vanadium during the calcination step. The tetravalent vanadium can be converted to pentavalent vanadium by calcining the precursor in a free oxygen-containing gas, such as air, at temperatures of about 300° to about 600° C. until about 20 to about 90 atom percent of the vanadium has been converted to pentavalent vanadium. If more than about 90 atom percent of the vanadium is converted to pentavalent vanadium, usually caused by calcining too long or at too high a temperature, the selectivity of the resultant catalyst, and consequently, the yield of maleic anhydride decrease. On the other hand, conversion of less than about 20 atom percent of the vanadium during air calcination does not seem to be beneficial. As will occur to those skilled in the art, the exact calcination conditions will depend on the method of preparing the precursor, equipment configurations, the particular pore modification agent or other additives to the precursor; however, it has been found that calcination at about 500° C. for about 4 hours is generally sufficient.

After the phophorus-vanadium-oxygen precursor containing the pore modification agent has been calcined, the catalyst thus formed is placed in a reactor used to convert hydrocarbons to maleic anhydride. Thereafter, a mixture of a hydrocarbon and a free oxygen-containing gas, such as air, can be contacted with the catalyst at temperatures between about 350° and 600° C. at concentrations of from about 1 to about 10 mole percent hydrocarbon at a space velocity up to 3000 cc/cc/hour to produce maleic anhydride.

However, as is well known in the art, the initial yield of maleic anhydride may be low, and if this is the case, the catalyst can be "conditioned" by contacting the catalyst with low concentrations of hydrocarbon in air at low space velocities for a period of time before production operations begin.

ANALYSIS OF THE CATALYST

After the catalysts of the present invention have been used for about 16 hours in production operations to convert saturated hydrocarbons to maleic anhydride, the catalysts are characterized by having a tetravalent vanadium content between about 20 and 100 atom percent. The pore volume of the catalyst from pores having diameters between about 0.8 micron and about 10 microns is greater than about 0.02 cc/g, and preferably greater than about 0.03 cc/g.

The pore volume is determined by measuring the amount of mercury that is forced into the interstices of the sample at about $10.55 \times 10^6$ kg/m$^2$ pressure. The pore volume resulting from pores having various sized diameters is determined by measuring the amount of mercury that is forced into the interstices of the catalyst sample at different pressures. For example, the pore volume of a sample from pores greater than 10 microns in diameter can be determined by measuring the amount of mercury that is forced into the interstices of the sample up to about $1.23 \times 10^4$ kg/m$^2$. The pore volume of a sample from pores having diameters between about 0.8 and 10 microns is determined by measuring the amount of mercury that is forced into the interstices of the sample at pressures between about $1.23 \times 10^4$ kg/m$^2$ and about $1.54 \times 10^5$ kg/m$^2$. The pore volume resulting from pores having diameters less than 0.8 micron is determined by measuring the amount of mercury that is forced into the interstices of the sample at pressures between about $1.54 \times 10^5$ kg/m$^2$ and $10.55 \times 10^6$ kg/m$^2$.

It has been found that most of the pore volume in catalysts made by prior art procedures and in the catalysts of the present invention results from pores having diameters less than 0.8 micron. Furthermore, catalysts made by prior art procedures have pore volumes less than about 0.01 cc/g from pores having diameters between about 0.8 micron and 10 microns. However, the catalysts of the present invention have pore volumes from pores having diameters between about 0.8 micron and about 10 microns greater than 0.02 cc/g, preferably greater than 0.03 cc/g, or even higher, say greater than 0.05 cc/g. Surprisingly, such catalysts were found to provide a higher yield of maleic anhydride than the prior art catalysts. Furthermore, it has been found that catalysts having a pore volume from pores having diameters larger than about 10 microns have virtually no effect on the yield of maleic anhydride using such catalysts. It is preferred to provide a catalyst wherein the pore volume from pores having diameters between about 1 micron and about 5 microns is greater than 0.01 cc/g, and more preferably greater than 0.03 cc/g.

PREPARATION OF MALEIC ANHYDRIDE

The catalysts of the present invention are useful in a variety of reactors to convert hydrocarbons to maleic anhydride. Both fluidized bed reactors and fixed-tube, heat-exchanger type reactors are satisfactory and the details of the operation of such reactors are well known to those skilled in the art. The reaction to convert hydrocarbons to maleic anhydride requires only contacting the hydrocarbons admixed with a free-oxygen containing gas, such as air or oxygen-enriched air, with the catalyst at elevated temperatures. The hydrocarbon/air mixture is contacted with the catalyst at a concentration of about 1 to about 10 mole percent hydrocarbon at a space velocity of about 100 to 3000 cc/cc/hour and at temperatures between about 300° and about 600° C. to provide high maleic anhydride yields.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

A large number of non-aromatic hydrocarbons having from 4 to 10 carbon atoms can be converted to maleic anhydride using the catalysts of the present invention. It is only necessary that the hydrocarbon contain not less than 4 carbon atoms in a straight chain. As an example, the preferred saturated hydrocarbon is butane, but isobutane which does not contain 4 carbon atoms in a straight chain, is not satisfactory for conversion to maleic anhydride although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the saturated hydrocarbons, unsaturated hydrocarbons can be used. The preferred unsaturated hydrocarbon is butene, but other unsaturated hydrocarbons within the scope of this invention include butadiene, the pentenes, the hexenes, the heptenes, the octenes, the nonenes, the decenes, or mixtures of any of these with or without butene. Cyclic compounds such as cyclopentane or cyclopentene or oxygenated compounds such as furan, dihydrofuran, or even tetrahydrofurfural alcohol are satisfactory. Furthermore, the aforementioned feedstocks are not necessarily pure substances, but can be technical hydrocarbons.

DESCRIPTION OF THE PREFERRED EMBODIMENTS

This invention is illustrated by, but not limited to, the following Examples.

EXAMPLE I

A phosphorus-vanadium-oxygen catalyst is prepared by adding 228 grams of 85 percent phosphoric acid and 173 grams of 97.6 percent phosphorus acid to a mixture of 340 grams of vanadium pentoxide and 1157 milliliters of water. The phosphorus to vanadium atom ratio is about 1.08:1. The mixture of vanadium and phosphorus compounds is placed in an autoclave which is then heated to 100° C. and thereafter sealed. The autoclave containing the vanadium and phosphorus compounds is heated to about 145° C. for about 4 hours. After the autoclave is cooled and opened, the phosphorus-vanadium-oxygen precursor is placed in an open dish casserole and evaporated to dryness in an oven at 120° C. Then, the remaining solids are ground to pass a 12 mesh sieve (U.S. Standard Sieve Size). To samples of the resulting powder, about 7.5 weight percent, based on the weight of the powdered sample, of different pore modification agents are added. The powdered sample and the pore modification agent are blended and the blended mixture is then formed into 0.47 cm. diameter tablets using 1 weight percent graphite as a pelletizing lubricant. After calcining for about 6 hours at 380° to 400° C., the samples with the different pore modification agents are analyzed individually. The following tabulation shows the pore volume distribution of the catalyst containing the pore modification agents:

| PORE MODIFICATION AGENT | TOTAL PORE VOLUME (cc/g) | PORE VOLUME (cc/g) 0.8–10 $\mu$ PORES | 0.8–10 $\mu$ PORES IN TOTAL PORE VOLUME (%) |
|---|---|---|---|
| None | 0.2293 | 0.0019 | 0.8 |
| Oxalic Acid | 0.2619 | 0.0227 | 8.7 |
| Adipic Acid | 0.2722 | 0.0245 | 9.0 |
| Citric Acid | 0.2586 | 0.0236 | 9.1 |
| Polyethylene[a] Glycol | 0.2681 | 0.0290 | 10.8 |
| Methylcellulose[b] | 0.2936 | 0.0510 | 17.3 |
| Pecan Shell Flour | 0.2605 | 0.0467 | 17.8 |
| Corn Starch | 0.2674 | 0.0503 | 18.8 |
| Soluble Starch | 0.2443 | 0.0486 | 19.9 |
| Methylcellulose[c] | 0.3143 | 0.0632 | 20.1 |

[a] molecular weight about 6,000
[b] viscosity of 100 centipoise for 2 g. methylcellulose dissolved in 100 ml. water
[c] viscosity of 4,000 centipoise for 2 g. methylcellulose dissolved in 100 ml. water

EXAMPLE II

The procedure of Example I is repeated except that 7.5 weight percent citric acid is dissolved in the mixture of vanadium and phosphorus compounds in water rather than blending the citric acid with the ground solids. The total pore volume is 0.2702 cc/g, and the pore volume resulting from pores having diameters between about 0.8 micron and about 10 microns is 0.0192 cc/g, and the volume of pores in the 0.8 to 10 micron range is 8.7 percent of the total pore volume.

EXAMPLE III

A phosphorus-vanadium-oxygen catalyst is prepared by adding 215 grams of 85 percent phosphoric acid and 173 grams of 97.6 percent phosphorous acid to a mixture of 340 grams of vanadium pentoxide and 1150 milliliters of water. The phosphorus to vanadium atom ratio is about 1.05:1. The mixture of vanadium and phosphorus compounds is placed in an autoclave which is then heated to about 100° C. and thereafter sealed. The autoclave containing the vanadium and phosphorus compounds is heated to about 145° C. for about 2 hours. After the autoclave is cooled and opened, the phosphorus-vanadium-oxygen precursor is placed in an open dish casserole and evaporated to dryness in an oven at 120° C. The remaining solids are ground to pass an 18 mesh sieve (U.S. Standard Sieve Size). To samples of the resulting powder, various levels of methylcellulose are added, and the powder and methylcellulose are blended. The blended mixture is formed into 0.47 cm. diameter tablets using 1 weight percent graphite as a pelletizing lubricant.

After calcining for about 5 hours at 380° to 400° C., the samples are tested by placing the tablets in a 1.9 cm. diameter, 15.24 cm. long, fixed-bed reactor which gives results comparable to those obtained in a production reactor. At a temperature of about 400° C., using a feed stream containing 1.5 mole percent butane-in-air, at a space velocity of about 1500 cc/cc/hour, the butane was converted to maleic anhydride. The following tabulation shows the pore volume distribution of the catalysts containing the methylcellulose and the yield of maleic anhydride after the catalysts have been used for at least 16 hours to convert butane to maleic anhydride:

| % METHYL-CELLULOSE | PORE VOLUME (cc/g) TOTAL | 0.8–10 $\mu$ PORES | 1–5 PORES | MALEIC ANHYDRIDE YIELD (%) |
|---|---|---|---|---|
| 0 | 0.2281 | 0.0055 | 0.0043 | 49.1 |
| 5 | 0.3022 | 0.0441 | 0.0387 | 53.0 |
| 7.5 | 0.3171 | 0.0561 | 0.0486 | 53.1 |
| 10 | 0.3374 | 0.0726 | 0.0657 | 52.6 |

EXAMPLE IV

The procedure of Example III is repeated except that various levels of Sterotex powdered lubricant (available from Capital City Products Co. of Columbus, Ohio, a division of Stokely-VanCamp, Inc.) is used instead of methylcellulose. Sterotex is hydrogenated cottonseed oil, which is a triglyceride of a mixture of $C_{14}$, $C_{16}$ and $C_{18}$ fatty acids. It has a melting point of about 62° C., a maximum acid value of 0.4 percent, and a maximum iodine value of 5. The $C_{18}$ chain length predominates.

After calcining the tablets at about 500° C. for about 4 hours, the tablets are tested as in Example III. The following results are obtained:

| STEROTEX (wt. %) | PORE VOLUME (cc/g) TOTAL | 0.8–10 $\mu$ PORES | 1–5 $\mu$ PORES | MALEIC ANHYDRIDE YIELD (%) |
|---|---|---|---|---|
| 4 | 0.295 | 0.0257 | 0.0205 | 53.7 |
| 8 | 0.218 | 0.0244 | 0.0110 | 51.8 |

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. As an example, the catalysts may contain a small amount of an additive element to improve the yield of maleic anhydride, or the catalysts may be prepared by using hydrochloric acid rather than phosphorous acid as the reducing agent for the pentavalent vanadium. Accordingly, modifications are contemplated which can be made without departing from the spirit of the described invention.

What is claimed is:

1. In a method of preparing a phosphorus-vanadium-oxygen catalyst wherein a phosphorus compound and a vanadium compound are brought together under conditions to provide a catalyst precursor having a phosphorus to vanadium atom ratio between about 0.5:1 and 2:1, and calcining the precursor at a temperature between about 300° and 600° C., the improvement which comprises adding to the precursor a sufficient amount of a pore modification agent selected from the group consisting of polymeric materials, cellulosic materials, monosaccharides, polysaccharides, hydrogenated vegetable oils and mixtures thereof to provide a catalyst wherein the pore volume from pores having diameters between about 0.8 micron and about 10 microns is greater than 0.02 cc/g.

2. In a method of claim 1 wherein from about 1 weight percent to about 30 weight percent, based on the weight of the dry precursor, of said pore modification agent is added to the precursor.

3. In a method of claim 1 wherein from about 2 weight percent to about 15 weight percent, based on the weight of the dry precursor, of said pore modification agent is added to the precursor.

4. In a method of claim 1 wherein said pore modification agent is methylcellulose.

5. In a method of claim 1 wherein said phosphorus to vanadium atom ratio is between about 1:1 and about 1.5:1, and from about 2 weight percent to about 15 weight percent of methylcellulose, based on the weight of the dry precursor, is added to the precursor.

* * * * *

UNITED STATES PATENT AND TRADEMARK OFFICE
CERTIFICATE OF CORRECTION

PATENT NO. : 4,092,269
DATED : May 30, 1978
INVENTOR(S) : Ramon A. Mount, John F. Pysz, Jr., Harold Raffelson It is certified that error appears in the above-identified patent and that said Letters Patent are hereby corrected as shown below:

Column 7, line 31, "catalyst" should read: --catalysts--.

Column 8, in the first Table, heading: "1-5" Pores should read: --1-5 µ Pores--.

Signed and Sealed this

Twenty-second Day of May 1979

[SEAL]

Attest:

RUTH C. MASON
*Attesting Officer*

DONALD W. BANNER
*Commissioner of Patents and Trademarks*